(12) United States Patent
Schaible et al.

(10) Patent No.: US 6,443,925 B1
(45) Date of Patent: Sep. 3, 2002

(54) BALLOON CATHETER SHAFT FORMED OF LIQUID CRYSTAL POLYMERIC MATERIAL BLEND

(75) Inventors: Stephen G. Schaible, Anaheim; Debashis Dutta, Santa Clara, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/394,656

(22) Filed: Sep. 13, 1999

(51) Int. Cl.[7] .................. A61M 29/00; A61M 25/00
(52) U.S. Cl. ..................... 604/96.01; 604/524
(58) Field of Search ............... 604/96, 101, 284, 604/280, 524–527; 606/192, 194

(56) References Cited

U.S. PATENT DOCUMENTS

| | | | |
|---|---|---|---|
| 4,867,174 A | * 9/1989 | Skribiski | 128/772 |
| 4,963,313 A | 10/1990 | Noddin et al. | 264/573 |
| 4,966,807 A | 10/1990 | Harvey et al. | 428/220 |
| 5,078,700 A | 1/1992 | Lambert et al. | 604/264 |
| 5,156,785 A | 10/1992 | Zdrahala | 264/108 |
| 5,182,334 A | * 1/1993 | Chen, Sr. et al. | 525/397 |
| 5,248,305 A | * 9/1993 | Zdrahala | 604/280 |
| 5,270,086 A | 12/1993 | Hamlin | 428/35.2 |
| 5,306,246 A | 4/1994 | Sahatjian et al. | 604/96 |
| 5,328,472 A | 7/1994 | Steinke et al. | 604/102 |
| 5,410,797 A | 5/1995 | Steinke et al. | 29/435 |
| 5,441,489 A | * 8/1995 | Utsumi et al. | 604/280 |
| 5,554,139 A | 9/1996 | Okajima | 604/282 |
| 5,647,848 A | 7/1997 | Jørgensen | 604/96 |
| 5,680,873 A | * 10/1997 | Berg et al. | 128/772 |
| 5,713,828 A | * 2/1998 | Coniglione | 600/7 |
| 5,783,633 A | * 7/1998 | Sperling et al. | 525/131 |
| 5,786,426 A | * 7/1998 | Sperling et al. | 525/131 |
| 5,807,327 A | * 9/1998 | Green et al. | 604/96 |
| 5,947,939 A | * 9/1999 | Mortier et al. | 604/280 |
| 5,951,494 A | * 9/1999 | Wang et al. | 600/585 |
| 5,951,539 A | * 9/1999 | Nita et al. | 604/526 |
| 5,961,511 A | * 10/1999 | Mortier et al. | 604/527 |
| 6,016,848 A | * 1/2000 | Egres, Jr. | 138/137 |
| 6,024,722 A | * 2/2000 | Rau et al. | 604/96 |

OTHER PUBLICATIONS www.ticona–us.com/Literature/documents/NPE2000, web site address for attached slides 1 and 11 from "Liquid Crystal Polymers" Jun. 20, 2000.

* cited by examiner

Primary Examiner—Sharon Kennedy
(74) Attorney, Agent, or Firm—Fulwider Patton Lee & Utecht, LLP

(57) ABSTRACT

A balloon catheter having at least part of the shaft thereof formed of a liquid crystal polymeric material. The liquid crystal polymeric material is preferably blended with a non-liquid crystal polymeric material, to form a polymer blend of at least 50 percent by weight liquid crystal polymeric material and the balance being essentially non-liquid crystal polymeric material. A catheter shaft formed from the polymer blend of the invention has improved strength, stiffness, and kink resistance.

15 Claims, 1 Drawing Sheet

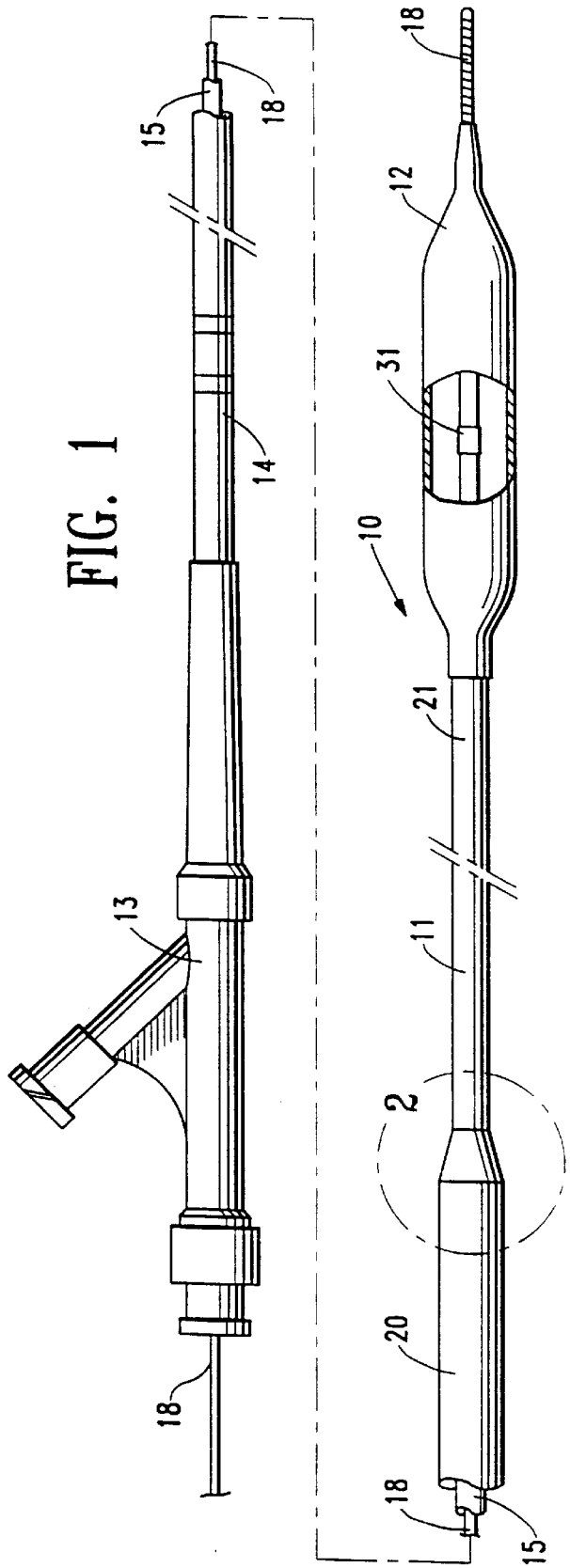
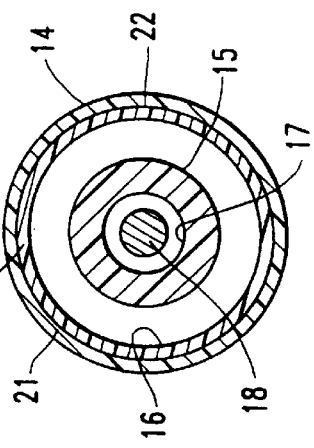
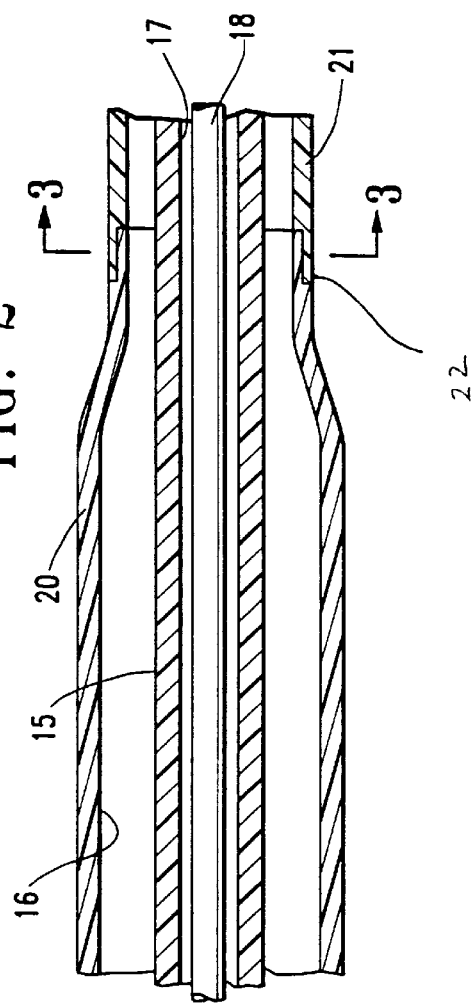

BALLOON CATHETER SHAFT FORMED OF LIQUID CRYSTAL POLYMERIC MATERIAL BLEND

BACKGROUND OF THE INVENTION

This invention relates to the field of intravascular catheters, and more particularly to a catheter having a shaft formed in part of a liquid crystal polymeric material (LCP).

Balloon catheters generally comprise a catheter shaft with a balloon on the distal end of the shaft, and are used in a number of procedures, such as percutaneous transluminal coronary angioplasty (PTCA). In PTCA the balloon catheter is used to restore free flow in a clogged coronary vessel. The catheter is maneuvered through the patient's tortuous anatomy and into the patient's coronary anatomy until the balloon is properly positioned across the stenosis to be dilated. Once properly positioned, the balloon is inflated with liquid one or more times to a predetermined size at relatively high pressures (e.g. greater than 4 atm) to reopen the coronary passageway.

High strength materials are commonly required in the design of catheter components. For example, to improve catheter maneuverability, the catheter shaft is typically provided with a relatively stiff proximal shaft section and a relatively flexible distal shaft section. The stiffened proximal shaft section provides greater push to the catheter which facilitates advancement over a guidewire. The stiffness also provides greater torqueability so that torque applied to the proximal end of the catheter extending outside of the patient results in rotation of the distal tip of the catheter. However, for overall catheter performance, the proximal shaft stiffness must be balanced against the need to maintain a low profile and shaft flexibility. Stiffened proximal shaft sections are typically formed from stainless steel hypotube and polymeric materials, although pseudoelastic or elastic NiTi alloys may also be used. However, these prior art materials have the drawbacks of high cost, or inadequate performance by being overly stiff in the case of hypotubing or inadequately stiff in the case of polymeric shafts.

Therefore, what has been needed is a balloon catheter with a stiffened shaft section having improved strength characteristics. The present invention satisfies these and other needs.

SUMMARY OF THE INVENTION

The invention is directed to a catheter which has at least part of the shaft thereof formed of a liquid crystal polymeric material. In a presently preferred embodiment, the catheter shaft is formed of a polymer formulation of at least 50 percent by weight liquid crystal polymeric material. In one embodiment, the liquid crystal polymeric material is blended with a non-liquid crystal polymeric material to form a polymer blend (hereafter, the LCP blend). In a presently preferred embodiment of the LCP blend, the LCP blend has at least 50 percent by weight and less than 100 percent by weight of the liquid crystal polymeric material. There are many suitable liquid crystal polymers that may be used, and a presently preferred example is VECTRA sold by Hoechst-Celanese. The non-liquid crystal polymeric material used in the LCP blend may be any extrudable thermoplastic polymer, and presently preferred examples are polyester copolymers such as HYTREL available from Du Pont de Nemours, and PEEK available from Victrex.

A catheter shaft formed from the LCP blend of the invention has improved stiffness. The LCP acts as reinforcement in the polymer matrix, similar to braided fiber reinforcements used in catheter shaft construction but at significantly improved cost and ease of manufacture.

Liquid crystal polymers exhibit crystalline behavior in the liquid phase such that the liquid phase molecules retain some of the orientational order of the solid phase. The molecular orientation improves the strength of a polymeric component in the direction of orientation. The extent of molecular orientation can be expressed in terms of the aspect ratio, which is the ratio of the length of the liquid crystal polymer fibrils to the diameter of the fibrils. The aspect ratio is a factor of the draw-down ratio, which is the ratio of the diameter of the die to the diameter of the finished extrudate, used during extrusion. Liquid crystal polymers can be made to solidify after extrusion with an even greater degree of molecular orientation than ordinary polymers, and thus can be used to form ultra high strength articles. However, the high molecular orientation may result in disadvantageous characteristics in a catheter shaft, such as a low elongation and little ability to withstand loads applied transverse to the orientation direction. These disadvantages are avoided by the polymer blend of the invention. Thus, the catheter shaft of the invention formed of a polymer blend of at least 50% by weight liquid crystal polymeric material with a non-liquid crystal polymeric material provides improved shaft strength and stiffness characteristics.

One presently preferred embodiment of the invention is a dilatation catheter which has an elongated catheter shaft with a relatively stiff proximal section formed of the LCP blend and a relatively flexible distal section and an inflatable dilatation member on a distal portion of the catheter. Conventional catheter design may be used, including over the wire, fixed wire and rapid exchange designs, having a single shaft with dual lumens or a multimembered shaft with inner and outer tubular members.

A catheter shaft formed from the polymer blend of the invention has improved strength, stiffness, and kink resistance. These and other advantages of the invention will become more apparent from the following detailed description of the invention and the accompanying exemplary drawings.

DESCRIPTION OF THE DRAWINGS

FIG. 1 is an elevational view partially in section of a balloon catheter which embodies features of the invention.

FIG. 2 is a longitudinal cross-sectional view of the shaft of the catheter shown in FIG. 1, in circle 2.

FIG. 3 is a transverse cross-sectional view of the shaft shown in FIG. 2 taken along lines 3—3.

DETAILED DESCRIPTION OF THE INVENTION

As shown in FIG. 1 the balloon catheter 10 of the invention generally includes an elongated catheter shaft 11 with an inflatable balloon 12 on a distal portion of the catheter shaft and an adapter 13 mounted on the proximal end of the catheter shaft.

The catheter shaft has an outer tubular member 14 and an inner tubular member 15 disposed within the outer tubular member and defining with the outer tubular member annular lumen 16 which is in fluid communication with the interior of the inflatable balloon 12. The inner tubular member 15 has an inner lumen 17 extending therein which is configured to slidably receive a guidewire 18 suitable for advancement through a patient's coronary arteries. The distal extremity of the inflatable balloon 12 is sealingly secured to the distal extremity of the inner tubular member 15 and the proximal extremity of the balloon is secured to the distal extremity of the outer tubular member 16.

In the embodiment illustrated in FIG. 1, the outer tubular member 14 has a relatively stiff proximal shaft section 20 formed of the polymer formulation of the invention having at least 50 weight percent liquid crystal polymeric material. The outer tubular member 14 has a distal shaft section 21, formed of a more flexible extrudable polymeric material, including but not limited to polyethylene, HYTREL, nylons, polyether block amide (PEBAX), or polyethylaneterephthalate (PET). The distal extremity of the proximal shaft section 20 is secured to the proximal extremity of the distal shaft section 21 by suitable means such as heat or laser fusion or commercially available cyanoacrylate adhesive. In the embodiment illustrated in FIG. 1, the proximal shaft section 20 tapers to a smaller outer diameter which is joined to the distal shaft section 21 at lap joint 22. However, a variety of suitable configurations may be used to join the proximal shaft section 20 to the distal shaft section 21. The inner tubular member extends the length of the catheter and may be formed of suitable materials, including but not limited to polyethylene, HYTREL, PEBAX, nylon, or the like.

In the embodiment illustrated in FIG. 1, the polymer formulation is a LCP blend of a major amount of a liquid crystal polymeric material and a minor amount of a non-liquid crystal polymeric material, having at least 50 percent by weight liquid crystal polymeric material and a balance of essentially non-liquid crystal polymeric material. The LCP blend has a weight percent of liquid crystal polymeric material less than 100 weight percent, and preferably from about 60 to about 90 weight percent of the blend. In a presently preferred embodiment, the LCP blend is about 75 weight percent liquid crystal polymeric material and about 25 weight percent non liquid crystal polymeric material. The non-liquid crystal polymeric material is an extrudable thermoplastic engineering polymer. A presently preferred non liquid crystal polymeric material is a polyester elastomer such as HYTREL. A suitable grade of HYTREL is the HYTREL 8238 grade polymer. However, many suitable non-liquid crystal polymers exist, including, polyetheretherketone (PEEK), polyethylene sulfone (PES), polyphenylene sulfide (PPS), PET, polybutylene terephthalate (PBT), polyetherimide (PEI), polyamide, polyether block amides (PEBA), polyolefins, and fluoropolymers such as polyvinylidene fluoride (PVDF), polytetrafluoroethylene (PTFE), poly(ethylene-chlorotrifluoroethylene) (ECTFE), poly(ethylene-tetrafluoroethylene) (ETFE), fluorinated ethylene-propylene (FEP), polyvinyl fluoride (PVF), and perfluoroalkoxy (PFA). Fillers such as PTFE and carbon fibers may be used in the LCP blend.

The LCP blend of the invention produces a balloon catheter proximal shaft section with improved strength, stiffness, and kink-resistance. The LCP blend of the proximal shaft section has a tensile strength greater than about 8,000 psi, and preferably about 20,000 psi, and a tensile modulus greater than about 300 kpsi, and preferably about 1500 kpsi. The elongation is typically about 20% to about 200%, and preferably about 20% to about 50%. The kink resistance of the shaft is reflected in the amount of curvature that can be imparted in the shaft before it will kink. A catheter shaft formed from the 75 percent liquid crystal polymeric material/25 percent HYTREL blend of the invention can form a 5 cm diameter circle before kinking.

The catheter shaft can be produced using conventional extrusion processes, such as in-line or cross-head methods. The aspect ratio of the LCP fibers in the extruded catheter shaft is about 10 to about 100, and preferably about 50 to about 100. The extrusion process may use a fixed die and mandrel, or may use a rotating die and/or mandrel to impart radial orientation in the LCP fibers of the extrudate. When a fixed die and mandrel is used, the draw down ratio is greater than 100, and typically greater than about 500.

In the LCP blend for the catheter shaft, the liquid crystal polymeric material is a separate phase from the non liquid crystal polymeric material of the blend. Suitable liquid crystal polymeric materials are copolyesters, such as those sold under the trade name VECTRA, and polyesteramides such as XYDAR. In a presently preferred embodiment, the liquid crystal polymeric material and matrix polymeric material are temperature-melt (T-melt) compatible, so that the polymers melt in the same temperature range. The T-melt compatibility is desirable because it avoids the polymer degradation that may otherwise result during extrusion. The length of the dilatation catheter 10 may be about 120 to about 150 cm in length, and typically is about 135 cm in length. The outer tubular member 14 has an OD of about 0.03 to about 0.05 inch (0.76–1.27 mm) and an ID of about 0.025 to about 0.035 inch (0.635–0.899 mm). The outer tubular member 14 may taper in its distal portion to a smaller OD of about 0.04 to about 0.02 inch (1.02–10.55 mm) and a smaller ID of about 0.03 to about 0.015 inch (0.762–0.381). The smaller diameter portion between the taper and the proximal extremity of the balloon 12 may be about 5 to about 25 cm in length.

The inner tubular member 15 has an OD ranging from about 0.018 to about 0.026 inch (0.457–0.66 mm), and the ID of the inner tubular member will usually be determined by the diameter of the guidewire 18 which is to be used with the catheter, which may range from about 0.008 to about 0.02 inch (0.203–0.51 mm). The inner diameter of the inner lumen should be about 0.002 to about 0.005 inch (0.051–0, 127 mm) larger than the OD of the guidewire 18 to be used. Usually there will be a family of catheters for each size of guidewire with a variety of maximum inflated balloon sizes, e.g., 0.5 to about 4 mm in diameter and with various working lengths ranging from about 1 to about 10 cm.

To the extent not previously described herein, the various catheter components may be formed of conventional materials. For example, radiopaque marker 31 may be a gold band and the adapter body may be formed of polycarbonate polymers.

While the present invention has been described in terms of certain preferred embodiments, those skilled in the art will recognize that modifications and improvements may be made to the invention without departing from the scope thereof. For example, while the use of the LCP blend for a catheter shaft was discussed in terms of a proximal section of an outer tubular member, the LCP blend may be used for various catheter shaft sections, including a proximal section of the inner tubular member.

What is claimed is:

1. A balloon catheter, comprising:
   a) a catheter shaft having a proximal end, a distal end, and at least one lumen therein, and having a proximal shaft section and a distal shaft section, at least one of the shaft sections being formed of a polymer blend comprising at least 50 percent by weight of a liquid crystal polymeric material; and
   b) an inflatable member on a distal portion of the catheter shaft.

2. The catheter of claim 1 wherein the proximal shaft section is formed of the polymer blend.

3. The catheter of claim 1 wherein the polymer blend comprises an extrudable non-liquid crystal polymeric material blended with the liquid crystal polymeric material.

4. The catheter of claim 3 wherein the liquid crystal polymeric material is less than about 100 weight percent of the polymer blend.

5. The catheter of claim 3 wherein the liquid crystal polymeric material is between about 60 weight percent to about 90 weight percent of the polymer blend.

6. The catheter of claim 3 wherein the liquid crystal polymeric material is about 75 weight percent of the polymer blend.

7. The catheter of claim 2 wherein the polymer blend of the proximal shaft section has a tensile strength of about 60,000 psi and a tensile modulus of about 3,000,000 psi.

8. The catheter of claim 1 wherein the liquid crystal polymeric material forms elongated fibers having an aspect ratio of not less than 10.

9. The catheter of claim 3 wherein the non-liquid crystal polymeric material is an extrudable thermoplastic engineering polymer.

10. The catheter of claim 9 wherein the thermoplastic engineering polymer is selected from the group consisting of polyetherketone, polyethyleneterepthalate, polyethersulfone, polyamide, polyetherblockamide, polyester elastomers, polyolefin, and fluoropolymers.

11. The catheter of claim 1 wherein the liquid crystal polymeric material is a polyester.

12. The catheter of claim 1 wherein the shaft includes an outer tubular member having a proximal shaft section and an inner tubular member disposed within a lumen of the outer tubular member, and the proximal shaft section of the outer tubular member is formed of the polymer blend.

13. A balloon catheter, comprising:

a) a catheter shaft having a proximal end, a distal end, and at least one lumen therein, and having a proximal shaft section which is formed of a polymer blend including liquid crystal polymeric material, and a distal shaft section which extends to a location proximal to a distal end of the catheter and which is formed of a polymeric material not including a liquid crystal polymeric material; and b) an inflatable member on a distal portion of the catheter shaft.

14. The balloon catheter of claim 13 wherein the inflatable member is secured to the distal shaft section.

15. The balloon catheter of claim 13 wherein the proximal shaft section is formed of a polymer blend of at least 50 percent by weight liquid crystal polymeric material.

* * * * *

UNITED STATES PATENT AND TRADEMARK OFFICE
CERTIFICATE OF CORRECTION

PATENT NO.    : 6,443,925 B1
DATED         : September 3, 2002
INVENTOR(S)   : Stephen G. Schaible et al.

It is certified that error appears in the above-identified patent and that said Letters Patent is hereby corrected as shown below:

<u>Title page,</u>
Item [56], U.S. PATENT DOCUMENTS, add:
-- 6,242,063    6/2001  Ferrera et al.
   6,284,333    9/2001  Wang et al. --.

<u>Column 4,</u>
Line 17, the sentence starting with "The" should be a new paragraph.

Signed and Sealed this

Fifteenth Day of April, 2003

JAMES E. ROGAN
*Director of the United States Patent and Trademark Office*